US011467070B2

(12) United States Patent
Trombetta et al.

(10) Patent No.: US 11,467,070 B2
(45) Date of Patent: Oct. 11, 2022

(54) POROUS MATERIAL FOR THE INCLUSION OF CYTOLOGIC PREPARATIONS, PROCESS FOR OBTAINING THE SAME AND ITS USE

(71) Applicants: UCS Diagnostic S.r.l., Morlupo (IT); Universitè Campus Bio-Medico di Roma, Rome (IT)

(72) Inventors: Marcella Trombetta, Rome (IT); Alberto Rainer, Rome (IT); Anna Crescenzi, Rome (IT); Chiara Taffon, Rome (IT); Pamela Mozetic, Rome (IT); Marco Costantini, Rome (IT); Antonio Santoro, Morlupo (IT)

(73) Assignees: UCS DIAGNOSTIC S.R.L., Morlupo (IT); UNIVERSITÀ CAMPUS BIO-MEDICO DI ROMA, Rome (IT)

( * ) Notice: Subject to any disclaimer, the term of this patent is extended or adjusted under 35 U.S.C. 154(b) by 839 days.

(21) Appl. No.: 16/345,019

(22) PCT Filed: Nov. 2, 2017

(86) PCT No.: PCT/IB2017/056812
§ 371 (c)(1),
(2) Date: Apr. 25, 2019

(87) PCT Pub. No.: WO2018/083616
PCT Pub. Date: May 11, 2018

(65) Prior Publication Data
US 2019/0277733 A1    Sep. 12, 2019

(30) Foreign Application Priority Data

Nov. 4, 2016 (IT) .......................... 102016000111352

(51) Int. Cl.
*G01N 1/00* (2006.01)
*G01N 1/36* (2006.01)
(Continued)

(52) U.S. Cl.
CPC ............. *G01N 1/36* (2013.01); *A01N 1/0231* (2013.01); *A61L 27/20* (2013.01); *A61L 27/52* (2013.01);
(Continued)

(58) Field of Classification Search
None
See application file for complete search history.

(56) References Cited

U.S. PATENT DOCUMENTS

2014/0219962 A1    8/2014    Zhang et al.

FOREIGN PATENT DOCUMENTS

CN    102585276 A1    7/2012
DE    10117234 A1    10/2002
(Continued)

OTHER PUBLICATIONS

International Search Report and Written Opinion for International Application No. PCT/IB2017/056812, dated Jan. 31, 2018, European Patent Office, Netherlands, 16 pages.
(Continued)

*Primary Examiner* — Jyoti Nagpaul
(74) *Attorney, Agent, or Firm* — Sterne, Kessler, Goldstein & Fox P.L.L.C.

(57) ABSTRACT

The present invention relates to a porous material for inclusion of cytological preparations such as for example the material taken from procedures of fine needle aspiration with high effectiveness level. The effectiveness consists in quantitative and qualitative advantages: the proposed porous material has a high affinity for the cellular material which is captured and kept in the meshes by forming a kind of tissue without losing cellular elements thus with a quantitative advantage with respect to the traditional methods. Moreover, the material proposed in the patent is provided with wide cells delimited by thin meshes, this allows a wide diffusion
(Continued)

of the fixative by optimizing the morphology preservation of the cytological sample; such qualitative advantage translates into optimum yield of the ancillary methods for studying the pathology.

17 Claims, 1 Drawing Sheet

(51) Int. Cl.
| | |
|---|---|
| *C08J 3/075* | (2006.01) |
| *G01N 1/31* | (2006.01) |
| *A61L 27/56* | (2006.01) |
| *G01N 1/30* | (2006.01) |
| *A61L 27/52* | (2006.01) |
| *A61L 27/20* | (2006.01) |
| *A01N 1/02* | (2006.01) |
| *A61B 10/02* | (2006.01) |
| *C08L 5/08* | (2006.01) |
| *G01N 31/22* | (2006.01) |

(52) U.S. Cl.
CPC ............... *A61L 27/56* (2013.01); *C08J 3/075* (2013.01); *G01N 1/30* (2013.01); *G01N 1/31* (2013.01); *A61B 10/02* (2013.01); *C08J 2305/08* (2013.01); *C08L 5/08* (2013.01); *G01N 31/22* (2013.01); *G01N 2001/364* (2013.01)

(56) References Cited

FOREIGN PATENT DOCUMENTS

| WO | WO-2004006961 A1 | 1/2004 |
|---|---|---|
| WO | WO-2018083616 A1 | 5/2018 |

OTHER PUBLICATIONS

Ji, C., et al., "Enhancing cell penetration and proliferation in chitosan hydrogels for tissue engineering applications," Biomaterials 32(36):9719-9729, Elsevier, Netherlands (2011).

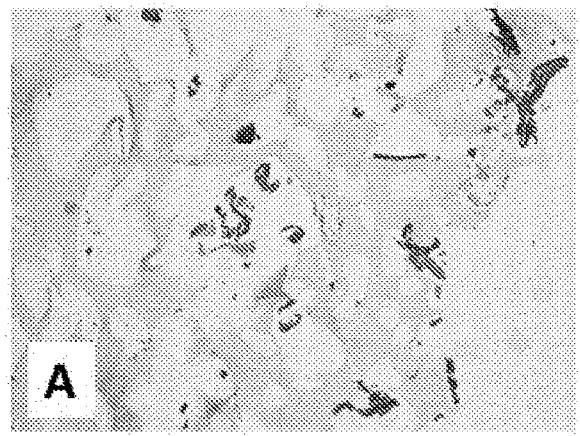
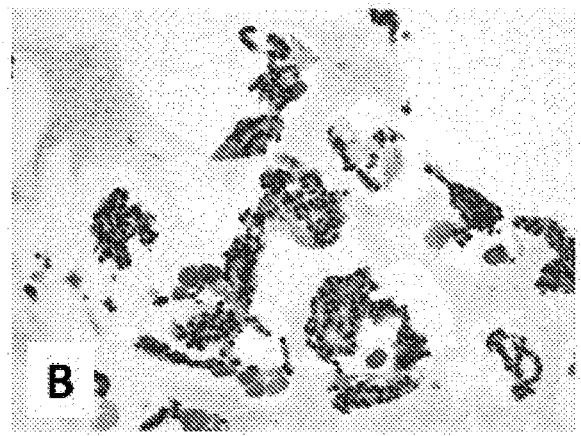
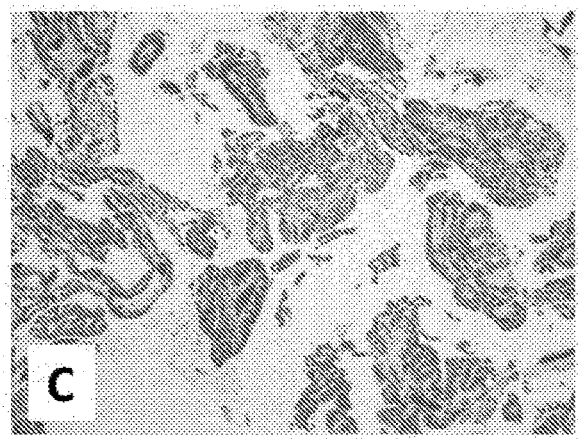
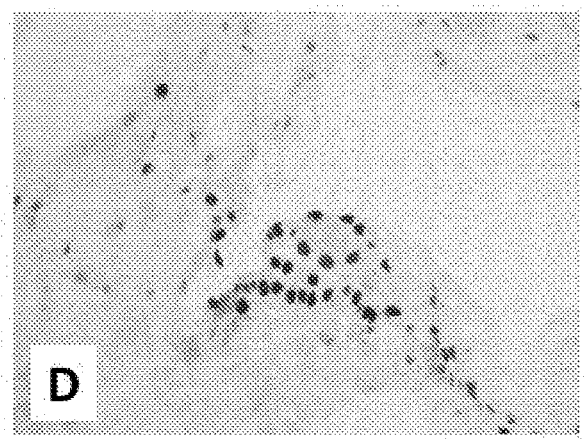

POROUS MATERIAL FOR THE INCLUSION OF CYTOLOGIC PREPARATIONS, PROCESS FOR OBTAINING THE SAME AND ITS USE

The present invention relates to a porous material for inclusion of cytological preparations such as for example the bioptic material from procedures of fine needle aspiration with high effectiveness level.

The material set forth by the present invention has a high affinity for the cellular material, which is kept inside the meshes of the same, by maximising the yield. The material, loaded with the cellular infiltrate, can be subjected to the conventional procedures of fixation with aldehydes, and the fixation process increases the stability of the preparation in analogy to a biological tissue. The preparation proves to be compatible with all histological techniques applicable to fixed tissues, as well as with the most advanced analyses providing the recovery of genetic material from histological slices.

STATE OF ART

The patent application U.S. Pat. No. 5,817,032 A (Means and method for harvesting and handling tissue samples for biopsy analysis) and U.S. Pat. No. 8,383,067B2 (Biopsy support with sectionable resilient cellular material) shows a porous material with cellular structure compatible with microtomy to ease positioning and keeping a tissue sample inside the "cassette".

The patent application WO 2010030358 A1 (Scaffold for tissue sample orientation) shows materials with hydrogel features allowing the orientation of tissue samples and the inclusion thereof for histological purposes.

The literature reports considerable examples wherein chitosan-based porous biomaterials, produced with different methods (foams, fibres, etc.) are used for purposes of tissue engineering and regenerative medicine [1] that is with the purpose of sowing living cells and allowing the growth thereof, by stimulating the morphogenesis of a neotissue, or as drug-releasing systems [2-3].

In particular, foams of chitosan can be produced with several foaming techniques, which include even microfluidic approaches [4].

The patent application EP 2394670 A1 (Chitosan-based biomimetic scaffolds and methods for preparing the same) shows a method for preparing scaffolds made of chitosan with at least 2 layers, at least one thereof constituted by fibres and at least one having a supporting porous structure. Mayall F G et al (*J Clin Pathol* 2011, 64, 818-819) describe a method for performing inclusions of cytological material from serous samples by using a gelatine foam; the process provides the centrifugation of the serous liquid and the removal of the supernatant, by obtaining a deposit of cells which is made to absorb on a layer of gelatine foam, followed by fixation in alcohol or formalin.

The patent application UK GB2499665A shows a device comprising a housing and a material for inclusion, wherein a housing end can be connected to a needle, whereas the material for inclusion is contained at least partially in said housing, by implementing a fluidic connection with said needle. In this way, the invention shows a process for the infiltration of cytological material in the material for inclusion during the fine needle aspiration procedure.

However, this technique demonstrated to be a little effective both in capturing the material aspirated during the maneuver, and in keeping such material during the procedures of fixation and inclusion in paraffin. In fact, the material capture is limited by the presence of random interconnections between the cells of the porous support which sometimes result to be not communicating and stop the progression of the aspirated material inside the support. The material not entered the support deposits on the surface and it is lost by detachment during dipping in formalin or subsequent processing steps. A support with good consistency to cutting in paraffin, but including a too poor amount in cells, is obtained.

The cytological analysis is a widely spread, cheap and reliable examination, for the pathological diagnosis, however it has the disadvantage of not keeping for long time the biological sample for subsequent analyses such as the immunohistochemistry characterization and the molecular tests which instead have become integral part of the report in many pathology areas. For this reason, hydrogels were introduced on the market, intended to include a "pellet" of cells (obtained by centrifugation), which could be processed by means of histological techniques, which provide the implementation of a "small block" of inclusion material including the sample, which can be kept, analogously to the histological tissues, fixed in formalin, included in paraffin and subjected to subsequent cutting procedures, with the purpose of obtaining slices whereon the microscopic surveys are to be carried out. The so-processed material is called cytoincluded or cell-block.

Since this technique is difficult, recently porous supports were developed intended to be directed infiltrated with cellular suspensions, with the purpose of obtaining a histological preparation from cytological material.

However, said supports have several limitations as the used polymeric substrate has different features from a tissue and it does not adapt well to the traditional histological techniques. Moreover, the preparations are characterized by low cellularity and poor affinity of the cellular infiltrate for the substrate.

It has surprisingly found that a chitosan-based porous structure increases the effectiveness of the process for keeping the cellular suspensions dispensed thereon. Therefore, the present invention relates to a chitosan-based porous material, processes for the production thereof and the use thereof as support for including eukaryote or prokaryote cells with the purpose of the processing thereof with histological inclusion techniques. The porous material according to the invention surprisingly shows a high affinity for the cellular material, which is kept inside the meshes of the same, by maximizing the yield. The material set forth by the present invention can be processed with standard histological techniques analogously to the biological tissues.

BRIEF DESCRIPTION OF THE FIGURES

Four figures are enclosed to the present invention, showing

FIG. 1 (A,B) Comparison between a commercial substrate and FIG. 1(C,D) the material set forth by the present invention.

A) Limited penetration and adhesion of the cellular material after infiltration of the commercial substrate. B) Non-specificity of a nuclear staining on histological slices obtained starting from the commercial substrate. C) Increased penetration and adhesion of the cells on the material set forth by the present invention. D) Optimum specificity of the nuclear staining on histological slices of the material set forth by the present invention after inclusion and cutting. FIG. 1, by way of example, shows a comparison between a commercial support CytoFoam (of the patent application UK GB2499665A) and the porous supports set forth by the present invention.

The commercial support shows a low cellularization and poor adhesion of the cellular material to the polymeric substrate (FIG. 1A). Moreover, the difficulty in processing the material is demonstrated by the strong aspecificity of the nuclear staining performed by immunohistochemical techniques (FIG. 1B). Contrary to the commercial material, the properties of the material set forth by the present invention increase the penetration of the cellular suspension and guarantee an optimum adhesion of the cellular material to the porous substrate (FIG. 1C). This reflects in a better result of the histological procedures, as it can be observed by the strong specificity of a nuclear staining performed by immunohistochemistry (FIG. 1D).

DETAILED DESCRIPTION OF THE INVENTION

The present invention relates to a process for the production of a porous material for inclusion of cytological preparations; the porous material substantially comprises foams made of chitosan and/or derivatives of chitosan with various level of derivatization.

The porous material according to the invention is obtained starting from a solution of chitosan and/or a lactosylated derivative thereof or a vinyl derivative of chitosan (alone or in mixture with a sulfhydryl derivative), having a molecular weight between 50 and 200 kDa, 100 kDa being the preferred molecular weight. Said chitosan or the lactosylated or vinyl derivatives thereof alone or in mixture with a sulfhydryl derivative are dissolved at a percentage between 0.1 and 4% weight/volume, 2% weight/volume being the preferred concentration, in an acid solution in a range of pH 2-6, constituted by a polar inorganic acid or by a polar organic acid; advantageously the lactic acid having 2% weight/volume is the preferred solvent. In a variant of the invention as chitosan solvent 2-(N-morpholine) ethanesulfonic acid can be used.

As lactosylated derivative of chitosan Chitlac can be mentioned, obtained by forming a Schiff base between a primary amino group existing along the chitosan chain and the aldehyde group existing in the open shape of the lactose reducing end, with 5-70% derivation level; as vinyl derivative of chitosan the methacrylate chitosan can be mentioned, obtained by methacrylation reaction with methacrylate anhydride, with 5-40% derivation level; suitable sulfhydryl derivatives can be prepared by reaction of primary amines of chitosan with mercaptan acids, such as for example mercaptoethane acid, mercaptopropanoic acid, etc., catalysed by carbodiimides/succinimmides, with 5-40% derivatization level. In the second step of the process according to the invention (procedure b, gelification), in case of a solution of chitosan or a lactosylated derivative thereof, the solution is gelified by using a crosslinking agent, which can be constituted by a dialdehyde at a concentration of 0.03-0.05% (weight/volume of total), advantageously 0.04% glutaraldehyde.

The step of gelification by using a crosslinking agent provides the establishment of a limited number of crosslinks involving the free amino groups of chitosan, and it has the only function of providing mechanical stability to the gel, whereas most part of the amino groups (up to 90%) are made available for the subsequent reaction with the biological material.

Advantageously the gelification takes place inside moulds, in a preferred embodiment with parallelepiped shape having a squared base. In another preferred embodiment, said moulds have cylindrical shape. In another variant the moulds have the final shape of the object to be obtained. The porous material can be shaped in porous structures of large dimensions, such as slabs or blocks, from which the inclusion supports in the final shape are obtained by means of cutting procedures.

In case of a solution of a vinyl derivative of chitosan (alone or in mixture with a sulfhydryl derivative), the gelification is carried out by photopolymerization by adding a photoinitiator and exposure to a UV source. Advantageously said photoinitiator is Irgacure 2959 in concentration of 0.5-2.0% by weight and the exposure to said UV source takes place at a wavelength of 250-405 nm and at a dose between 0.1 and 20 $J/cm^2$.

The gelification—in case of a vinyl derivative of chitosan (alone or in mixture with a sulfhydryl derivative)—can take place by radical polymerization by heating at temperatures between 30 and 70° C., 50° C. being the preferred temperature, in presence of a radical catalyst, the preferred catalyst being ammonium persulphate at the concentration of 0.2-1.5% by weight.

At the end of procedure b), in all above-described variants of the process a hydrogel is obtained.

In order to obtain the porous material according to the invention one proceeds with a procedure of freeze-drying—according to techniques known in the art—the obtained hydrogel. The freeze-drying in case can be preceded by a series of washing phases of the hydrogel in water or buffer solutions at neutral pH, with the purpose of neutralizing the acidity thereof.

In order to better adjust the effects of freeze-drying on the porosity of obtained material, in the invention process the following variants can be carried out which, too, are set forth by the present invention.

According to a first variant, for adjusting the porous structure prior to the gelification procedure inside solution of chitosan and/or derivatives thereof a ionic or non-ionic surfactant at a concentration between 0.01% and 2% is added and inert gas is blown, for example nitrogen.

According to an additional variant, prior to the gelification procedure inside the solution of chitosan and/or the derivatives thereof a ionic or non ionic surfactant at a concentration between 0.01% and 2% is added under stirring as well as a non polar liquid, advantageously pure cyclohexane, by producing an oil-in-water emulsion comprising as continuous phase the solution and as dispersed phase the non-polar liquid. The dispersed phase is extracted after the gelification of the continuous phase by means of lower alkyl alcohols, advantageously ethanol. The ionic or nonionic surfactant (such as for example tyloxapol added at a concentration between 0.01% and 2%) carries out the function of stabiliser of foam/emulsion.

The porous material which can be obtained by the process according to the invention has interconnected pores with sizes between 5 and 700 μm and a total porosity (volumetric fraction) between 40 and 90%.

The material set forth by the invention can be used for the inclusion of cytological preparations for histological diagnosis techniques as such o following inclusion in paraffin, acrylic, polyurethane, epoxy resins, means of cold inclusion. As a consequence, the above-shown procedures can be used for the production of supports for inclusion directly with the wished shape, by using moulds with suitable sizes.

Porous structures with big sizes (slabs or blocks) can be further produced, from which the inclusion supports in the final shape are obtained by means of cutting procedures.

The so-obtained supports for inclusion are supplied with cells obtained by a fine needle aspiration procedure, followed by fixation with a suitable fixation agent, such as paraformaldehyde (from 1 to 4%) or glutaraldehyde (from 0.1 to 5%). By way of example and not for limitative purpose, said cells can derive from pathological nodules of thyroid, lung, mamma, liver (metastatic lesions), pancreas, lymph nodes and salivary glands.

The supports are further suitable to be used in cytology from sediment by including, by way of example and not for limitative purpose, ascites, pleural effusions and spontaneous urines. Such procedure provides the supply of the support with cells existing in the sediment of a biological fluid subjected to centrifugation.

It is to be underlined that, in case of the present invention, the porous support participates in the fixation reaction by creating cross-links between the cells and the material itself thanks to the reactive groups made available downwards the previously illustrated synthesis and forming procedures, and this translates into an increased stability of the histological preparation which shows processability features similar to a biological tissue. In particular, the cells placed on the matrix surface at time of collecting the organ are incorporated in the caveolae and kept herein during fixation. The fixed preparation then can be processed with the usual histological techniques of state of art for biological tissues including: inclusion in paraffin, acrylic, polyurethane, epoxy resins, means of cold inclusion (such as for example Shandon Cryomatrix) and afterwards subjected to the usual histological analyses including: histological staining (not limited to hematoxylin, eosin, Masson's thrichrome, von Kossa, safranin O, toluidine blue, AdipoRed, etc.), immunohistochemistry, immunofluorescence, immunogold, SEM and TEM microscopy. The supports show presence of cellular material for 7-8 sectioning levels on the average, showing that it is possible to obtain material in several sections for different studies. In all cases the cellular morphology resulted to be of high quality by preserving dyeing properties of the cellular components (basophilia and acidophily) and with high resolution in displaying the characters of diagnostic findings (nuclear membrane, nucleoli, cytoplasmic vacuoles). The structure of the supports after cutting appears microscopically in form of net having meshes with thin thickness which leave whole display of the cells included inside the fissures.

The porous supports are further effective in carrying out mutational molecular analyses on the included cytological material. The sections in paraffin can be sparefined, rehydrated and collected by means of blade of sterile scalpel in a test tube for DNA extraction according to the state of art. The quality of the extracted DNA, evaluated by means of the ratio of the absorption values at 260 and 280 nm at the spectrophotometer, shows values between 1.6 and 2 and the supports apparently do not interfere with the extraction, purification and amplification reactions.

The porous material according to the invention can be contained inside housings ("cassettes") for use in combination with automated processing systems.

Examples

Three applications of the material set forth by the present invention are provided by way of example and not for limitative purposes.

Immunohistochemical Characterization of Thyroid Nodules

The simple fine needle aspiration of the nodular lesion, in fact, has the limit of not succeeding in differentiating benign follicular proliferations from the malign ones, reason therefor the literature proposes the use of a panel of antibodies which increases sensitivity and examination specificity. Since several antibodies are to be treated, it is necessary to have available multiple sections in paraffin of the fine-needle-aspirated material and the International guidelines state textually that the availability of a cytoincluded is required [5].

The material set forth by the present invention is supplied with the material from fine needle aspiration, then it is subjected to fixation by immersion in 4% formalin or other fixative for cytology for 8-12 hours.

For preparing the slides, the fixed support is subjected to dehydration by means of a growing series of alcohols (ethanol by 30%, 50%, 70%, 95% 2×100%, each one 20 minutes) and xilene (2×30 minutes), prior to be infiltrated in melt paraffin at 56° C. The support then is subjected to inclusion in paraffin block sectioned at microtome (thickness 4-5 μm). The slices are recovered and placed on a slide according to a conventional method, sparefined and brought to water by means of decreasing series of alcohols. The matrix capability of keeping the extracellular material is particularly important, which in some cases represents an important diagnostic key and which instead is often lost during the preparation of the cytological inclusions with traditional methods. For example the colloid in the fine needle aspirations of the thyroid nodules results to be well kept and valuable.

The following staining procedures are carried out:
  hematoxylin/eosin (according to provider's protocol) to detect the preparation morphology.
  TTF1 nuclear marker by means of human anti-TTF1 mouse antibody (30 minutes at room temperature) and secondary anti-mouse antibody conjugated with polymer system.
  Gal3 cytoplasmic marker by means of human anti-Gal3 mouse antibody (30 min at RT) and secondary anti-mouse antibody conjugated with polymer system.

Immunohistochemical Characterization of Lung Nodules

The lung neoplastic pathology requires an accurate characterization of the neoplastic cells, which assumes indispensable character in the not operable cancers wherein the therapeutic choice is based upon the profile of the histotype and of the mutational attitude evaluated in the aspirated material [6]. The preparation protocol shown previously is repeated until obtaining sections on slide, thereon the following staining procedures are carried out: hematoxylin/eosin and immunohistochemistry for TTF1, p40, CK7 and CD56 by using anti-man mouse antibodies.

Capture of Cells from Sediment of Peritoneal Washings

Another important application field is the use of the support, set forth by the patent, for capturing the cells from sediment of peritoneal washings. Such procedure, which the surgeon performs during operations for abdominal cancers, requires an accurate evaluation as the presence of neoplastic cells, even if in minimum amount, changes in the pejorative sense the patient staging [7]. The traditional cytology has a very low sensitivity in detecting few and insulated neoplastic cells in the peritoneal washings.

The liquid coming from washing is centrifuged at 1800 revolutions per minute for 15 minutes. After having removed the supernatant, a sediment drop is deposited on the support. The preparation shown previously for preparing the slides is followed, which are used for the following staining procedures: hematoxylin/eosin and immunohistochemistry for CEA, calretinin, BerEP4 by using anti-man mouse antibodies.

BIBLIOGRAPHY

1. Croisier F, Jérôme C, Chitosan-based biomaterials for tissue engineering. European Polymer Journal 49 (2013) 780-792.
2. Takeshi Ikeda, Kahori Ikeda, Kouhei Yamamoto, et al., "Fabrication and Characteristics of Chitosan Sponge as a Tissue Engineering Scaffold," BioMed Research International, vol. 2014, Article ID 786892, 8 pages, 2014. doi:10.1155/2014/786892.
3. Foda N H, El-laithy H M, Tadros M I. Optimization of biodegradable sponges as controlled release drug matrices. I. Effect of moisture level on chitosan sponge mechanical properties. Drug Dev Ind Pharm. 2004 April; 30(4):369-79.
4. Testouri, C. Honorez, A. Barillec, D. Langevin and W. Drenckhan, Highly Structured Foams from Chitosan Gels, Macromolecules, 2010, 43 (14), pp 6166-6173.
5. 2015 American Thyroid Association Management Guidelines for Adult Patients with Thyroid Nodules and Differentiated Thyroid Cancer. The American Thyroid Association Guidelines Task Force on Thyroid Nodules and Differentiated Thyroid Cancer. THYROID Volume 26, Number 1, 2016
6. Frank Schneider, M D, Matthew A. Smith, M D, Molly C. Lane, Liron Pantanowitz, M D, Sanja Dacic, M D, PhD, and N. Paul Ohori, M D. Adequacy of Core Needle Biopsy Specimens and Fine-Needle Aspirates for Molecular Testing of Lung Adenocarcinomas. Am J Clin Pathol February 2015; 143:193-200.
7. Sobin L H, Gospodarowicz M, Wittekind C. TNM Classification of Malignant Tumours. Wiley-Blackwell; 2009.

The invention claimed is:

1. A process for the production of a porous material for inclusion of cytological preparations comprising the following steps of:
   a. arranging a chitosan and/or a lactosylated chitosan solution or a vinyl derivative solution of chitosan, said vinyl derivative being alone or in mixture with a sulfhydryl derivative of chitosan, all compounds having a molecular weight between 50 and 200 kDa and being dissolved in an acid solution of polar inorganic or organic acid;
   b. gelifying said solution to obtain a hydrogel, and
   c. freeze-drying of said hydrogel to obtain the porous material.

2. The process according to claim 1, wherein in said solution the chitosan and/or lactosylated chitosan or the vinyl derivative of chitosan, said vinyl derivative being alone or in mixture with the sulfhydryl derivative, are present at a concentration between 0.1 and 4% weight/volume and said acid solution is at a pH between 4 and 6.

3. The process according to claim 1, wherein the gelification is carried out by adding a crosslinking agent in an amount of 0.03-0.05% weight/volume, to said solution of chitosan and/or lactosylated chitosan.

4. The process of claim 3, wherein the crosslinking agent is a dialdehyde.

5. The process according to claim 1, wherein the gelification is carried out by photopolymerization through addition to said solution of a vinyl derivative solution of chitosan, said vinyl derivative being alone or in mixture with a sulfhydryl derivative of chitosan, of a photoinitiator and exposure to a UV source.

6. The process according to claim 5, wherein said vinyl derivative of chitosan is chitosan methacrylate, said photoinitiator is Irgacure 2959 in concentration of 0.5-2.0% by weight and the exposure to said UV source takes place at a wavelength of 250-405 nm and at a dose between 0.1 and 20 J/cm2.

7. The process according to claim 1, wherein the gelification is carried out by radical polymerization through heating of said solution of a vinyl derivative solution of chitosan, alone or in mixture with a sulfhydryl derivative of chitosan, at temperatures between 30 and 70° C., in presence of a radical catalyst, advantageously ammonium persulphate, at the concentration of 0.2-1.5% by weight.

8. The process according to claim 1, wherein prior to the gelification inside of said solution a ionic or non-ionic surfactant at a concentration between 0.01% and 2% is added and inert gas is blown into said solution.

9. The process according to claim 1, wherein
   a. prior to the gelification inside of said solution an ionic or non-ionic surfactant at a concentration between 0.01% and 2% is added as well as a nonpolar liquid thereby producing an oil-in-water emulsion comprising as continuous phase said solution and as dispersed phase said non-polar liquid, and
   b. said dispersed phase is extracted after the gelification of the continuous phase by means of lower alkyl alcohols.

10. The process of claim 9, wherein the nonpolar liquid is cyclohexane.

11. The process according to claim 1, wherein before said freeze-drying step said hydrogel is neutralized through rinse in water or in neutral-pH buffer.

12. The process according to claim 1, wherein the gelification step is carried out in molds having the final shape of the object to be obtained.

13. The porous material obtainable by the process of claim 1 having interconnected pores with sizes between 5 and 700 µm and a total porosity, such as volume fraction, between 40 and 90%.

14. The porous material according to claim 13, shaped in porous structures of large dimensions from which the inclusion supports in the final shape are obtained by means of cutting operations.

15. The porous material according to claim 13 contained inside housings for use in combination with automated processing systems.

16. A method of histological diagnosis comprising:
   preparing a cytological preparation by combining the porous material of claim 13 with paraffin, acrylic, polyurethane, epoxy resins, or means of cold inclusion; and
   analyzing the cytological preparation.

17. The method of claim 16, wherein said methods of histological diagnoses further include staining, immunohistochemistry, immunofluorescence, immunogold, scanning electron microscopy (SEM) and transmission microscopy (TEM).

* * * * *